United States Patent
VanDusseldorp

[19]

[11] Patent Number: 5,919,190
[45] Date of Patent: Jul. 6, 1999

[54] CUTTING LOOP FOR AN ELECTROCAUTERY PROBE

[76] Inventor: Gregg A. VanDusseldorp, 2177-A Greenvalley Dr., Lake County, Crown Point, Ind. 46307

[21] Appl. No.: 08/863,858

[22] Filed: May 27, 1997

Related U.S. Application Data

[60] Provisional application No. 60/033,713, Dec. 20, 1996.
[51] Int. Cl.⁶ ................................................. A61B 17/39
[52] U.S. Cl. ............................... 606/46; 606/41; 606/45; 606/49
[58] Field of Search .......................................... 606/41–50

[56] References Cited

U.S. PATENT DOCUMENTS

| | | | |
|---|---|---|---|
| 1,930,214 | 10/1933 | Wappler | 174/89 |
| 2,018,335 | 10/1935 | Wappler | 174/89 |
| 2,090,923 | 8/1937 | Wappler | 128/303.15 |
| 3,939,839 | 2/1976 | Curtiss | 128/303.15 |
| 3,973,568 | 8/1976 | Iglesias | 128/303.15 |
| 4,060,087 | 11/1977 | Hiltebrandt et al. | 128/303.15 |
| 4,116,198 | 9/1978 | Roos | 128/303.15 |
| 4,917,082 | 4/1990 | Grossi et al. | 606/46 |
| 4,931,047 | 6/1990 | Broadwin et al. | 604/22 |
| 5,078,716 | 1/1992 | Doll | 606/47 |
| 5,192,280 | 3/1993 | Parins | 606/48 |
| 5,282,799 | 2/1994 | Rydell | 606/48 |
| 5,395,363 | 3/1995 | Billings et al. | 606/41 |
| 5,415,656 | 5/1995 | Tihon et al. | 606/46 |
| 5,486,173 | 1/1996 | Vancaillie | 606/45 |
| 5,569,244 | 10/1996 | Hahnen | 606/46 |
| 5,582,610 | 12/1996 | Grossi et al. | 606/46 |
| 5,586,990 | 12/1996 | Hahnen et al. | 606/170 |
| 5,749,870 | 5/1998 | Gloth et al. | 606/45 |
| 5,766,168 | 6/1998 | Mantell | 606/46 |
| 5,782,829 | 7/1998 | Swiantek et al. | 606/46 |

OTHER PUBLICATIONS

Storz; "The World of Endoscopy"; 2nd Edition, Jan. 1994, 2 pgs. RES.ELSA and RES–S1.

*Primary Examiner*—Jack W. Lavinder
*Assistant Examiner*—David Ruddy
*Attorney, Agent, or Firm*—Domenica N.S. Hartman; Gary M. Hartman

[57] ABSTRACT

A cutting loop (212) for an electrocautery probe (210). The cutting loop (212) includes a conductor member having a cutting portion (214) with a proximal edge (214a) and a distal edge (214b), the proximal edge (214a) being adapted for creating an incision, i.e., resecting human tissue as the cutting loop (212) is traversed in a cutting direction approximately perpendicular to the proximal face (212a). During the resection procedure, the cutting portion defines a cutting plane that is generally parallel to the surface of the tissue being resected. The proximal face (214a) of the cutting portion (214) is characterized as flat or blunt, and is oriented to be substantially perpendicular to both the cutting direction and the cutting plane. The flat or blunt shape of the proximal face (214a) enhances the current distribution characteristics of the cutting loop (212). Preferably, the conductor member is generally U-shaped and the cutting portion (214) has a substantially rectangular cross-section, such that the proximal and distal faces (214a, 214b) of the cutting portion (214) are substantially parallel to each other. The rectangular cross-section of the cutting portion (214) may be substantially uniform, or may be variable along the length of the cutting portion (214). According to the invention, the rectangular cross-section of the cutting portion (214) further promotes the enhanced current distribution of the cutting loop (212). The conductor member may include a trailing portion (216) adjacent and spaced apart from the cutting portion in the cutting plane.

12 Claims, 3 Drawing Sheets

CUTTING LOOP FOR AN ELECTROCAUTERY PROBE

CROSS REFERENCE TO RELATED APPLICATIONS

This application claims the benefit of U.S. Provisional Application No. 60/033,713, filed Dec. 20, 1996.

BACKGROUND OF THE INVENTION

1. Field of the Invention

The present invention generally relates to electrosurgical probes. More particularly, this invention relates to a cutting loop for an electrocautery probe, wherein the cross-section of the cutting loop is tailored to enhance the performance of the probe through attaining a balance between the mass and surface area of the loop, yielding an enhanced current distribution such that resection and coagulation can be performed simultaneously, rapidly and to a desired degree with the probe.

2. Description of the Prior Art

Electrosurgical resection is a procedure in which damaged, diseased or enlarged tissue is removed with an electrocautery probe. An example is transurethral resection of the prostate (TURP), in which prostate tissue is removed by means of an electrocautery probe (e.g., a cutting loop) that is passed through the urethra by means of a resectoscope. This procedure has served as the historical treatment of benign prostate hypertrophy (BPH), cancer and prostatitus. Another example is endometrial ablation, which is an electrosurgical alternative treatment to hysterectomy in women with menorrhagia (abnormal uterine bleeding). In this case, an electrosurgical probe is passed through the vagina by means of a hysteroscope.

As understood by those skilled in the art, ablation and resection are electrosurgical effects accomplished by applying a highly damped radio frequency (RF) current to the tissue through an electrosurgical probe. Such current has been found to cut and/or coagulate tissue depending on power and wave length combinations. The active tip of the electrosurgical probe is in direct view of the surgeon at all times through the telescope which is part of the resectoscope. Electrosurgical probes have been available for some time in a number of shapes and sizes. U.S. Pat. No. 4,917,082 to Grossi et al. illustrates a number of resectoscope electrode (probe) types such as coagulating electrodes, knife electrodes, punctate electrodes, and roller electrodes. Another probe known in the art is referred to as a resectoscope loop electrode, and is used for TURP and other procedures. As shown in FIG. 1, this type of electrode 10 consists of an electrically-conductive U-shaped wire loop 12 supported between a pair of electrically-conductive arms 13. Notably, the wire loop 12 has a round cross-section along its entire length. Electrodes of the type shown in FIG. 1 have been available from numerous surgical equipment companies for about thirty years.

Resectoscope loop electrodes of the type described above provide adequate tissue cutting characteristics and adequate cutting speed, but with little or no coagulation affect, thereby allowing operative and post operative bleeding. Operative bleeding requires the constant attention of the surgeon to coagulate bleeders in order to prevent excess blood loss. Addressing the operative bleeding problem can account for a majority of the time required for the entire operation, and may necessitate changing electrodes (e.g., from the loop electrode to a coagulating roller-type electrode) numerous times during the procedure to control blood loss. Surgeons may blend electrosurgical cutting and coagulating current in an attempt to enhance coagulation during cutting, but in doing so reduce the cutting efficiency of the electrode, increase operative time, and may affect patient safety. In these cases, medical professionals may elect to increase power from the electrosurgical generator to maintain acceptable performance and decrease operative time. This tactic increases the potential for electrical shock to both patient and surgeon, and may cause premature electrode failure.

More recently, an electrode disclosed in U.S. Pat. No. 5,569,244 to Hahnen, available under the name WEDGE LOOP from Microvasive, has been available for use in endometrial ablation and prostatic resection. Shown in cross-section in FIG. 2, Hahnen discloses a U-shaped cutting loop 112 that is said to vaporize and resect tissue 118 while at the same time coagulating the tissue 118 in the resected area to avoid operative and postoperative bleeding. As shown, the cutting loop 112 is substantially triangular in cross-section, having sharp edges 112A at the intersection of the intersecting surfaces. The edge 112A portrayed in FIG. 2 as making the incision is termed the proximal edge because of its proximity to the electrode and its operator. The term "proximal" can also be seen as relative to the cutting direction during the resection procedure, when the cutting loop 112 is drawn toward the operator such that the proximal edge defines a cutting plane generally parallel to the surface of the tissue 118. The flat surface opposite the proximal edge is termed the distal edge of the cutting loop 1 12. The terms "proximal edge" and "distal edge" will be used consistently hereinafter in accordance with their above-noted accepted definitions.

While the cutting loop 112 depicted in FIG. 2 is said to have increased surface area for providing increased coagulation during resection, its triangular shape 112 creates drag or resistance to passing of the loop 112 through tissue, as depicted in FIG. 2. In addition, the mass of the cutting loop 112 is relatively high, requiring more power for the resection procedure. The combination of increased power and the irregular shape of the cutting loop 112 can burn and char the tissue, creating a poor quality pathology chip 120 as shown in FIG. 2.

As a result of the above-noted performance deficiencies, the cutting loop 112 of Hahnen must be moved very slowly through tissue to achieve adequate performance, which increases operative time. Since operative time is limited to the maximum safe time that the patient can withstand anesthesia, trauma, etc., the slow performance of Hahnen's triangular-shaped cutting loop 112 limits the area of tissue that can be treated. In such cases, medical professionals may elect to increase power from the electrosurgical generator to maintain acceptable speed and performance in order to decrease operative time. As was noted previously with the prior art round cutting loop 12, increasing the power to the triangular cutting loop 112 increases the potential for electrical shock to both patient and surgeon, further decreases the quality of the pathology chip, and may cause premature electrode failure.

Thus, it would be desirable if an improved cutting loop for an electrocautery probe was available for performing electrosurgical resection procedures, wherein the cutting loop promoted the performance of the probe such that resection and coagulation can be performed simultaneously, rapidly and to a desired degree.

SUMMARY OF THE INVENTION

It is an object of this invention to provide a cutting loop for an electrosurgical probe, such as a resectoscope, wherein the cutting loop is characterized by an enhanced current distribution such that resection and coagulation can be performed simultaneously and rapidly with the probe.

It is a further object of this invention that the enhanced current distribution of the cutting loop is achieved by forming the loop to have a flat or blunt cutting face in the cutting direction of the probe.

It is another object of this invention that the cutting loop has a substantially rectangular-shaped cross-section in at least that portion of the loop performing the resection incision, thereby promoting the enhanced current distribution of the loop through balancing the relationship between the mass of the loop and the surface area of the loop.

In accordance with a preferred embodiment of this invention, these and other objects and advantages are accomplished as follows.

According to the present invention, there is provided a cutting loop for an electrocautery probe. The cutting loop includes a conductor member having a cutting portion with a proximal face and a distal face, the proximal face being adapted for creating an incision, i.e., resecting human tissue as the conductor member is traversed in a cutting direction approximately perpendicular to the proximal face.

During the resection procedure, the cutting portion defines a cutting plane that is generally parallel to the surface of the tissue being resected. The proximal face of the cutting portion is generally blunt or flat and oriented to be substantially perpendicular to both the cutting direction and the cutting plane. As such, the term "face" as used herein merely serves to identify the fore and aft extremities of the cutting portion relative to the cutting direction, and does not necessitate a sharp edge, such as the sharp edges 112A of the prior art cutting loop 112 of FIG. 2. To the contrary, the proximal face of this invention can be characterized as blunt or flat, and therefore distinguishable from the sharp proximal edge 112A required by the prior art cutting loop 112. Furthermore, and according to this invention, the blunt or flat shape of the cutting portion provides in part for the enhanced current distribution characteristic of the cutting loop of this invention.

In a preferred embodiment of this invention, the conductor member is generally U-shaped and the cutting portion has a substantially rectangular cross-section in a plane perpendicular to the cutting plane and parallel to the cutting direction. As such, the proximal and distal faces of the cutting portion are parallel to each other, and the cutting portion further includes upper and lower surfaces that are substantially parallel to each other and substantially perpendicular to the proximal and distal faces. According to this invention, the rectangular cross-section of the cutting portion further promotes the enhanced current distribution of the cutting loop. The rectangular cross-section of the cutting portion may be substantially uniform, or may be variable along the length of the cutting portion. Also according to a preferred embodiment of this invention, the conductor member further includes a trailing portion adjacent and spaced apart from the cutting portion in the cutting plane, the trailing portion serving to attain even greater enhancement of the current distribution for the cutting loop. Further embodiments for the cutting loop of this invention include the presence of apertures formed in the cutting portion, a serrated proximal face defining a plurality of teeth projecting in the cutting direction in the cutting plane, and variations in the shape of the cutting portion that depart slightly from the general U-shape of the conductor member.

A significant advantage of the cutting loop of this invention is that the blunt shape of the proximal edge has been determined to significantly enhance the current distribution of the cutting loop to resection, and therefore enhances the performance of the probe such that resection and coagulation can be performed simultaneously, rapidly and to a desired degree. The preferred rectangular cross-section of the cutting portion of the loop further promotes this advantage, as does the presence of the rectangular-shaped trailing portion. Consequently, the cutting loop of this invention enables surgical procedure time to be reduced while simultaneously promoting safety for both the patient and the doctor performing the electrosurgical resection procedure.

Other objects and advantages of this invention will be better appreciated from the following detailed description.

BRIEF DESCRIPTION OF THE DRAWINGS

The present invention will now be described, by way of example, with reference to the accompanying drawings, in which.

DETAILED DESCRIPTION OF THE PREFERRED EMBODIMENT

Figure 3:
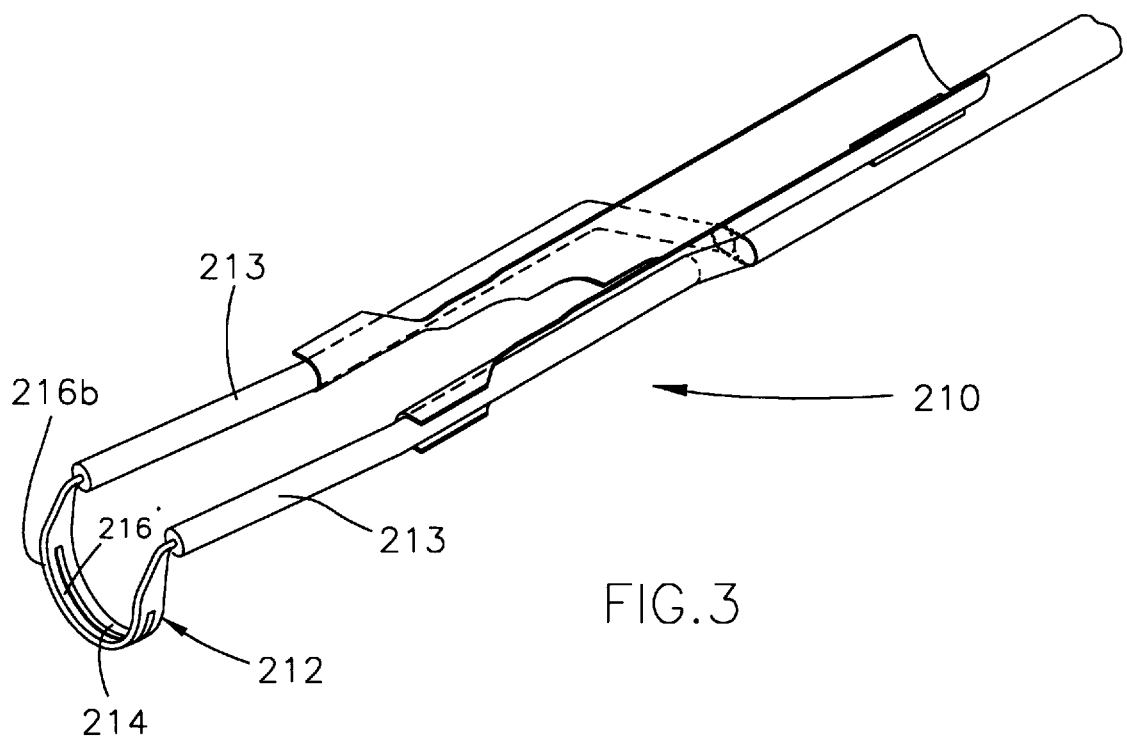
FIG. 3 is a perspective view of a resectoscope electrode or probe equipped with a cutting loop in accordance with a first embodiment of this invention.
Figure 4:
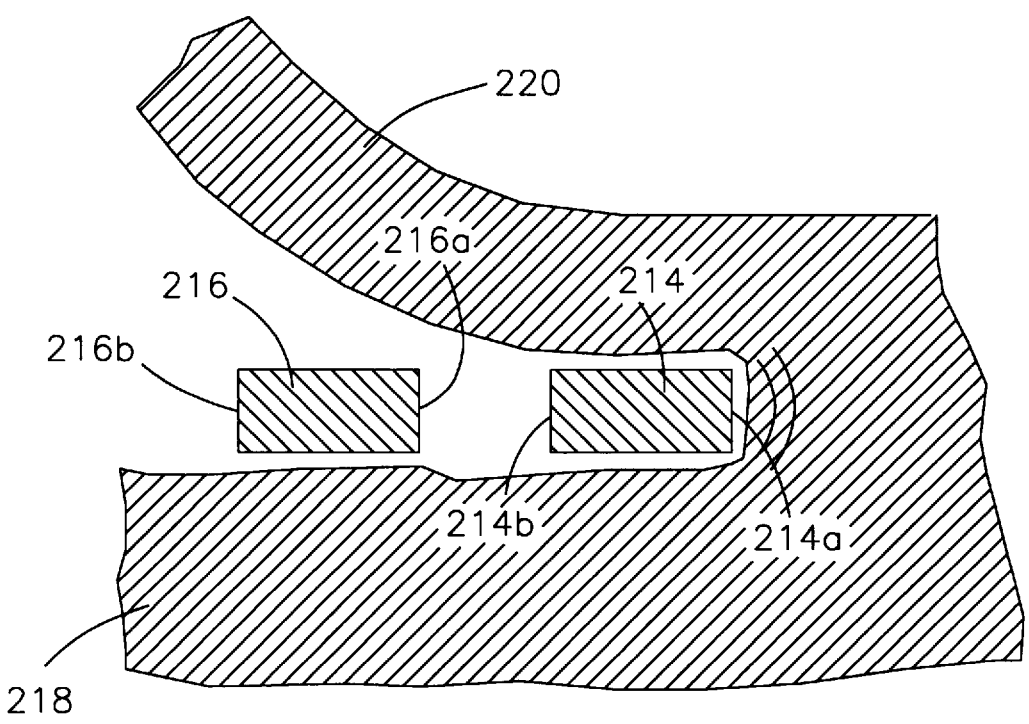
FIG. 4 depicts in cross-section a resection procedure using the cutting loop of FIG.3.
Figure 6:
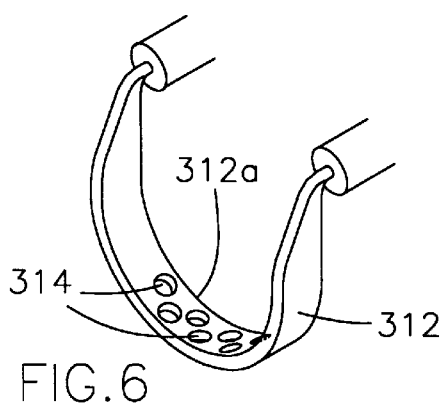
FIGS. 6, 7 and 8 show perspective views of cutting loops in accordance with alternative embodiments of this invention.
Figure 7:
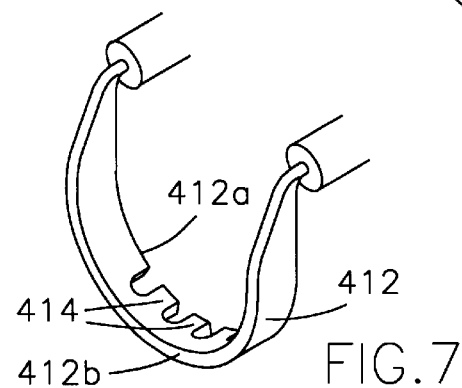
Figure 8:
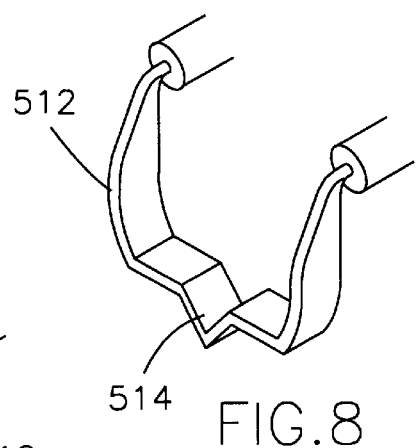

A resectoscope cutting loop 212 in accordance with a first embodiment of this invention is shown in FIGS. 3 and 4, with alternative embodiments of the cutting loop 212 shown in FIGS. 6 through 8. FIG. 3 shows the cutting loop 212 mounted to a resectoscope electrode or probe 210 that otherwise has a similar construction to the prior art electrode 10 of FIG. 1. The probe 210 is generally configured to include a pair of electrically-conductive arms 213 between and by which the cutting loop 212 is supported. As known in the art, the cutting loop 212 is also electrically-conductive, and may be constructed of any suitable conductive material, with a preferred material being a stainless steel.

According to the present invention, the resectoscope probe 210 is characterized by enhanced performance as a result of the geometry of the cutting loop 212, which is configured to promote the relationship between the mass, surface area and current distribution of the cutting loop 212. The advantageous result is that resection (cutting) and coagulation are able to occur simultaneously, rapidly and to a desired degree using a resectoscope probe or electrode equipped with the cutting loop 212 of this invention. As depicted in FIGS. 3 and 4, the cutting loop 212 according to the first embodiment of this invention includes a cutting member 214 and a trailing member 216. According to the invention, this geometrical configuration for the cutting loop 212 promotes an optimal balance between the mass, surface area and current distribution of the cutting loop 212, thereby providing for rapid cutting of tissue 218 with simultaneous coagulation and production of a high quality pathology chip 220, as depicted in FIG. 4.

While various embodiments of the cutting loop 212 are possible, such as by machining or fabricating an edge of the loop 212 to form slots, grooves, serrations, etc., as shown in FIGS. 6 through 8, in all cases the proximal (leading) face 214a of the cutting member 214 is specifically designed to be blunt or square and substantially perpendicular to both the cutting direction and the cutting plane defined as the cutting loop 212 traverses through the tissue 218 being resected. More preferably, the cutting and trailing members 214 and 216 are each substantially rectangular in cross-section and uniform in thickness, such that the proximal face 216a of the trailing member 216, as well as the distal (trailing) faces 214b and 216b of the cutting and trailing members 214 and 216, respectively, are also blunt or square and substantially perpendicular to both the cutting direction and the cutting plane. As a result of their rectangular cross-sections, the upper and lower surfaces of each member 214 and 216 are substantially perpendicular to the proximal and distal faces 214a, 214b, 216a and 216b, and therefore substantially parallel to the cutting plane.

As shown in FIG. 3, the cutting loop 212 of the first embodiment is actually a single U-shaped loop that is bifurcated along a cutting portion of the cutting loop 212 to form the cutting and trailing members 214 and 216. The rectangular cross-section of the trailing member 216 is preferably substantially identical to that of the cutting member 214, and trails the cutting member 214 as the cutting loop 212 is traversed through the tissue 218 in the cutting plane. Accordingly, the cutting and trailing members 214 and 216 are aligned in the direction of cut, as shown in FIG. 4, such that the trailing member 216 does not create drag through the tissue 218.

Figure 1:
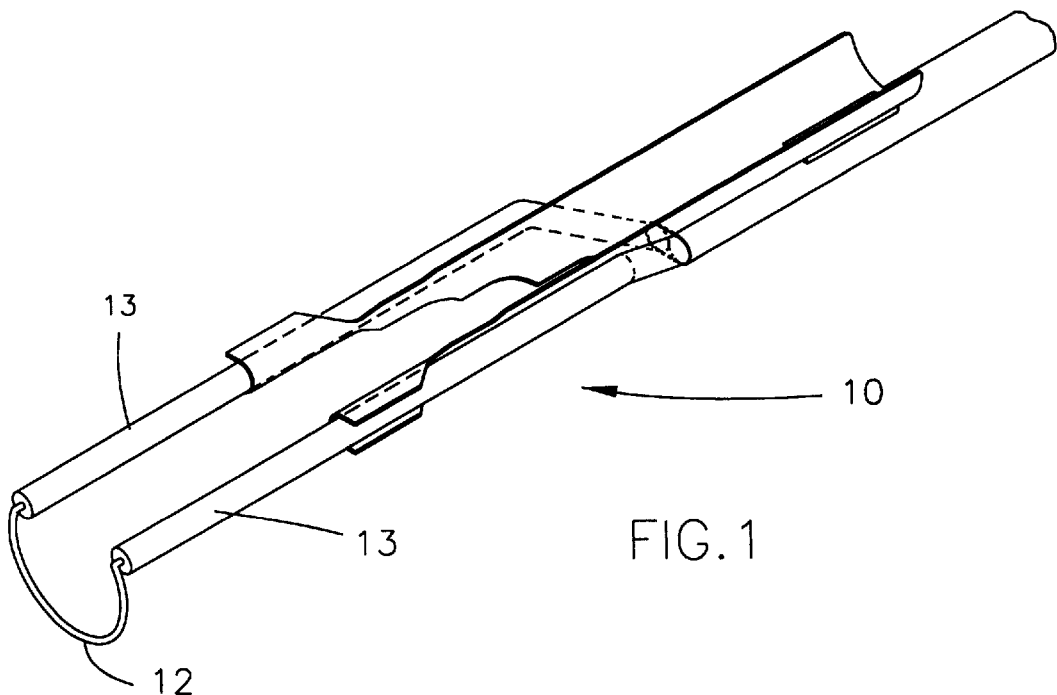
FIG. 1 is a perspective view of resectoscope electrode or probe equipped with a cuting loop having a circular cross-section in accordance with the prior art.
Figure 2:
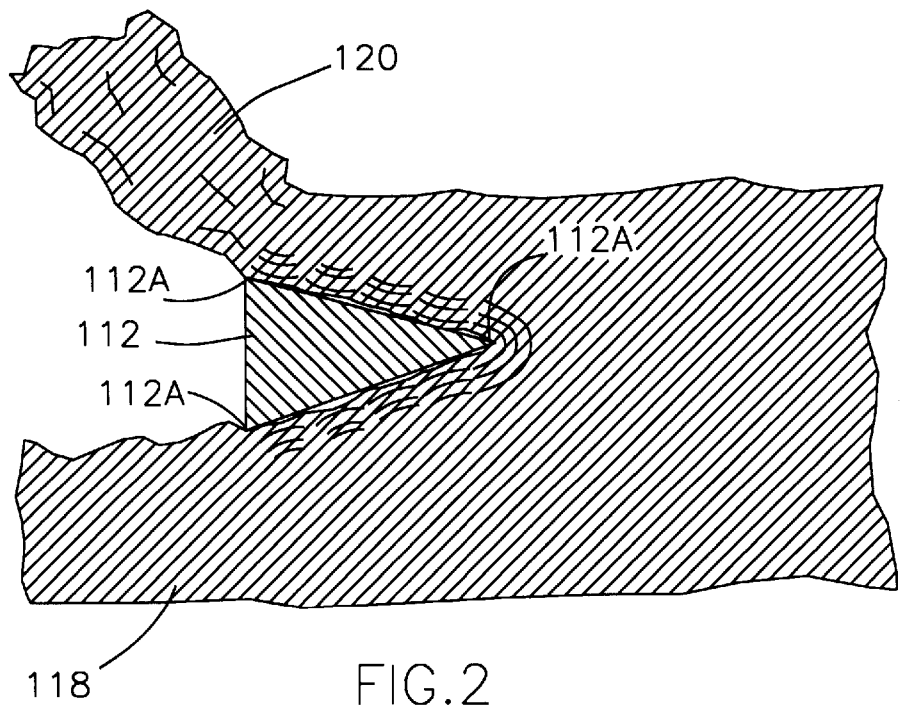
FIG. 2 depicts in cross-section a resection procedure using a triangular-shaped cutting loop in accordance with the prior art.
Figure 5A:
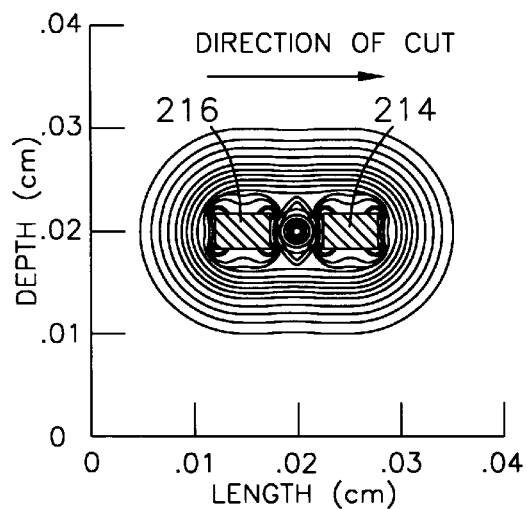
FIGS. 5A and 5B represents comparative current density distributions around the cutting loop of FIG. 4 and the cutting loop of FIG. 1, respectively.
Figure 5B:
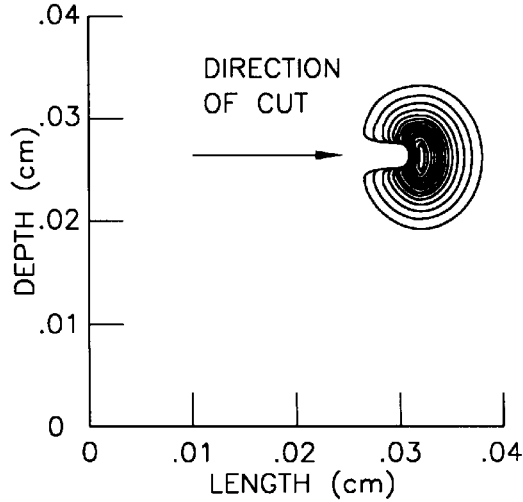

According to this invention, the cutting loop 212 of FIGS. 3 and 4 provides for balanced mass-surface area-current distribution characteristics that result in focused current concentration, providing a high degree of cutting efficiency with improved coagulation at normal "pure cut" current settings, and therefore eliminates the prior art practice of blending electrosurgical cutting and coagulating currents. In particular, the blunt or square cutting and trailing faces 214a, 214b, 216a and 216b of the members 214 and 216 have been determined to provide areas of focused high current concentration and distribution, as depicted in FIG. 5A, which are largely responsible for the enhanced performance of the cutting loop 212 portrayed in FIG. 4. The enhanced current concentration and distribution achieved by the cutting loop 212 of FIGS. 3 and 4 can be readily seen through a comparison of the current density distribution of the loop 212 with that of the prior art electrode 10 of FIG. 1, depicted in FIG. 5B. As seen from FIG. 5A, the current density distribution around the cutting loop 212 when completely immersed in human tissue is uniform and extends nearly one millimeter in every direction from the cutting and trailing members 214 and 216, whose dimensions are roughly 0.3 by 0.6 millimeter. In contrast, using the prior art cutting loop 12 having the same thickness as the cutting loop 212 depicted in FIG. 5A, the current density distribution can be seen in FIG. 5B as being concentrated toward the cutting direction, projecting less than 0.1 centimeter beyond the leading edge of the cutting loop 12.

Accordingly, FIG. 5A illustrates the superior current density distribution achieved by the cutting loop 212 of this invention, as compared to the round wire cutting loop 12 of the prior art electrode 10 of FIG. 1. The result of the superior current density distribution illustrated in FIG. 5A is the ability to make a rapid smooth cut with reduced operative and post operative bleeding, and the production of a high quality pathology chip. Testing has shown that, at equal power settings, the depth of coagulation produced by the cutting loop 212 of this invention is 45% greater than that of the prior art cutting loop 12 shown in FIG. 1. Importantly, these advantages enable a surgeon to treat normal and larger prostate glands while reducing surgical procedure time and safety concerns.

As noted above, cutting loops in accordance with this invention may be modified in various ways, yet retain the desired performance characteristics. FIGS. 6 through 8 show a few of many possible variations in the geometrical configuration for cutting loops in accordance with this invention. In all cases, the proximal and distal faces of the cutting portion of the loop, as well as faces machined or fabricated into the loop, such as slots, grooves, serrations, etc., are specifically configured to be blunt or square in order to achieve the desired current density distribution, and therefore the enhanced performance for the loop as described above. As is apparent from the Figures, the cross-section of each cutting loop, when taken in any plane that is parallel to the cutting direction and perpendicular to the cutting plane, is rectangular in shape.

FIG. 6 illustrates an embodiment of the invention in which a cutting loop 312 is formed to have apertures 314 extending through the loop 312 and substantially perpendicular to the proximal face 312a of the loop 312. A third embodiment of the invention is shown in FIG. 7, in which the proximal face 412a of a cutting loop 412 is shown as being serrated, forming a number of teeth 414 that extend parallel to and toward the cutting direction. Consequently, the rectangular cross-section of the cutting loop 412 is variable because the distance between the proximal and distal faces 412a and 412b, respectively, at each tooth 414 is greater than the distance between the distal face 412b and the root region between adjacent teeth 414. Notably, the leading edge of each tooth 414 is blunt and effectively forms the proximal face 412a of the cutting loop 412, such that each leading face is substantially perpendicular to the cutting direction and the cutting plane as required for the proximal faces of all cutting loops of this invention. In addition, each tooth 414 has oppositely-disposed side surfaces that are each approximately perpendicular to the proximal and distal faces 412a and 412b of the cutting loop 412 and substantially parallel to the cutting direction. The embodiment of FIG. 7 can be particularly useful under certain anatomical conditions, such as when performing a procedure on a patient that has undergone multiple prostate surgeries.

Finally, FIG. 8 shows a cutting loop 512 configured to include a trough 514 centered in the loop 512, which is suitable for use in removing tumors and polyps. Though the loop 512 is shown as being formed of a rectangular wire of uniform cross-section, the presence of this trough 514 causes the rectangular cross-section of the cutting loop 512 (again, taken in a plane parallel to the cutting direction and perpendicular to the cutting plane) to have a greater "thickness" along those portions of the loop 512 defining the sides of the trough 514, than those portions of the loop 512 that are substantially parallel to the cutting plane.

While the invention has been described in terms of a preferred embodiment, it is apparent that other forms could be adopted by one skilled in the art. For example, the shape, size and material for the cutting loop of this invention could differ from that noted. Accordingly, the scope of the invention is to be limited only by the following claims.

What is claimed is:

1. A cutting loop for an electrocautery probe, the cutting loop comprising a conductor member bifurcated between two opposite ends thereof so as to define a cutting portion and a trailing portion spaced apart from the cutting portion, the trailing portion being interconnected with the cutting portion only at the opposite ends of the conductor member so as to form a continuous slot therebetween, the cutting portion having a proximal face and a distal face, the proximal face having a uniform height and being planar between said opposite ends the proximal face being adapted for resecting human tissue as the conductor member is traversed in a cutting direction approximately perpendicular to the proximal face so as to produce a cutting plane approximately perpendicular to the proximal face, the proximal face having at least a portion which is substantially perpendicular to the cutting plane and the cutting direction.

2. A cutting loop as recited in claim 1, wherein the cutting portion of the conductor member has a substantially uniform rectangular cross-section.

3. A cutting loop as recited in claim 1, wherein the cutting portion has a lower surface and an upper surface parallel to and oppositely-disposed from the lower surface, the upper and lower surfaces of the cutting portion being substantially perpendicular to the proximal face of the cutting portion, the upper and lower surfaces of the cutting portion having at least portions that are not parallel to the cutting plane.

4. A cutting loop as recited in claim 1, wherein the trailing portion is spaced apart from the cutting portion in the cutting plane and adjacent the distal face of the cutting portion.

5. A cutting loop as recited in claim 1, wherein the trailing portion has a rectangular cross-section so as to define a proximal face, a distal face parallel to and oppositely-disposed from the proximal face, a lower surface, and an upper surface parallel to and oppositely-disposed from the lower surface, the trailing portion being adapted to trail the cutting portion as the conductor member is traversed in the cutting plane such that the proximal and distal faces of the trailing portion are substantially perpendicular to the cutting plane.

6. A cutting loop as recited in claim 5, wherein the cutting portion has a rectangular cross-section that is substantially identical to the rectangular cross-section of the trailing portion.

7. A cutting loop as recited in claim 1, further comprising a pair of arms from and between which the conductor member is supported.

8. A cutting loop as recited in claim 1, wherein the conductor member is substantially U-shaped so as to have two substantially straight portions interconnected with an arcuate portion, the cutting and trailing portions intersecting only within the straight portions of the conductor member.

9. A cutting loop for an electrocautery probe, the cutting loop comprising:

a pair of arms; and a substantially U-shaped conductor member supported by and between the pair of arms, the conductor member being bifurcated between two opposite ends thereof so as to define a cutting portion and a trailing portion that are interconnected only at the opposite ends of the conductor member so as to form a continuous slot therebetween, the cutting portion having a rectangular and uniform cross-section between said opposite ends so as to define a proximal face, a distal face parallel to and oppositely-disposed from the proximal face, a lower surface, and an upper surface parallel to and oppositely-disposed from the lower surface, the proximal face being adapted for resecting human tissue as the conductor member is traversed in a cutting direction in a cutting plane approximately parallel to the upper and lower surfaces such that the proximal and distal faces are substantially perpendicular to the cutting plane.

10. A cutting loop as recited in claim 9, wherein the cutting portion of the conductor member has a substantially uniform rectangular cross-section.

11. A cutting loop as recited in claim 9, wherein the trailing portion is spaced apart from the cutting portion in the cutting plane, adjacent the distal face of the cutting portion, and has a rectangular cross-section substantially identical to the rectangular cross-section of the cutting portion.

12. A cutting loop as recited in claim 9, wherein the conductor member has two substantially straight portions interconnected with an arcuate portion, the cutting and trailing portions intersecting only within the straight portions of the conductor member.

* * * * *